United States Patent [19]

Transue

[11] Patent Number: 5,437,643
[45] Date of Patent: Aug. 1, 1995

[54] SAFETY INTERPOSER FOR SURGICAL INSTRUMENTS

[75] Inventor: Deborah M. Transue, Bridgewater, N.J.

[73] Assignee: Ethicon, Inc., Somerville, N.J.

[21] Appl. No.: 183,095

[22] Filed: Jan. 18, 1994

Related U.S. Application Data

[62] Division of Ser. No. 61,973, May 17, 1993.

[51] Int. Cl.$^6$ ............................................. A61B 17/34
[52] U.S. Cl. ................................... 604/164; 606/185
[58] Field of Search ......... 606/185; 604/164, 164–169

[56] References Cited

U.S. PATENT DOCUMENTS 5,030,206 7/1991 Lander ................................ 604/164
5,114,407 5/1992 Burbank ............................. 604/164

FOREIGN PATENT DOCUMENTS 0537498 4/1993 European Pat. Off. ... A61B 17/072

*Primary Examiner*—Michael H. Thaler
*Attorney, Agent, or Firm*—Susan M. Schmitt

[57] ABSTRACT

Packaging for use in transportation and handling of a surgical instrument including a safety device which prevents engagement of the instrument or movement of a safety mechanism from a safety position. In a preferred embodiment the safety device is a safety interposer shaped to fit around the shaft of a trocar. The safety interposer acts as a physical barrier between the trocar and cannula of the trocar assembly and prevents the two parts from coupling which may occur from jostling during transportation or handling.

5 Claims, 5 Drawing Sheets

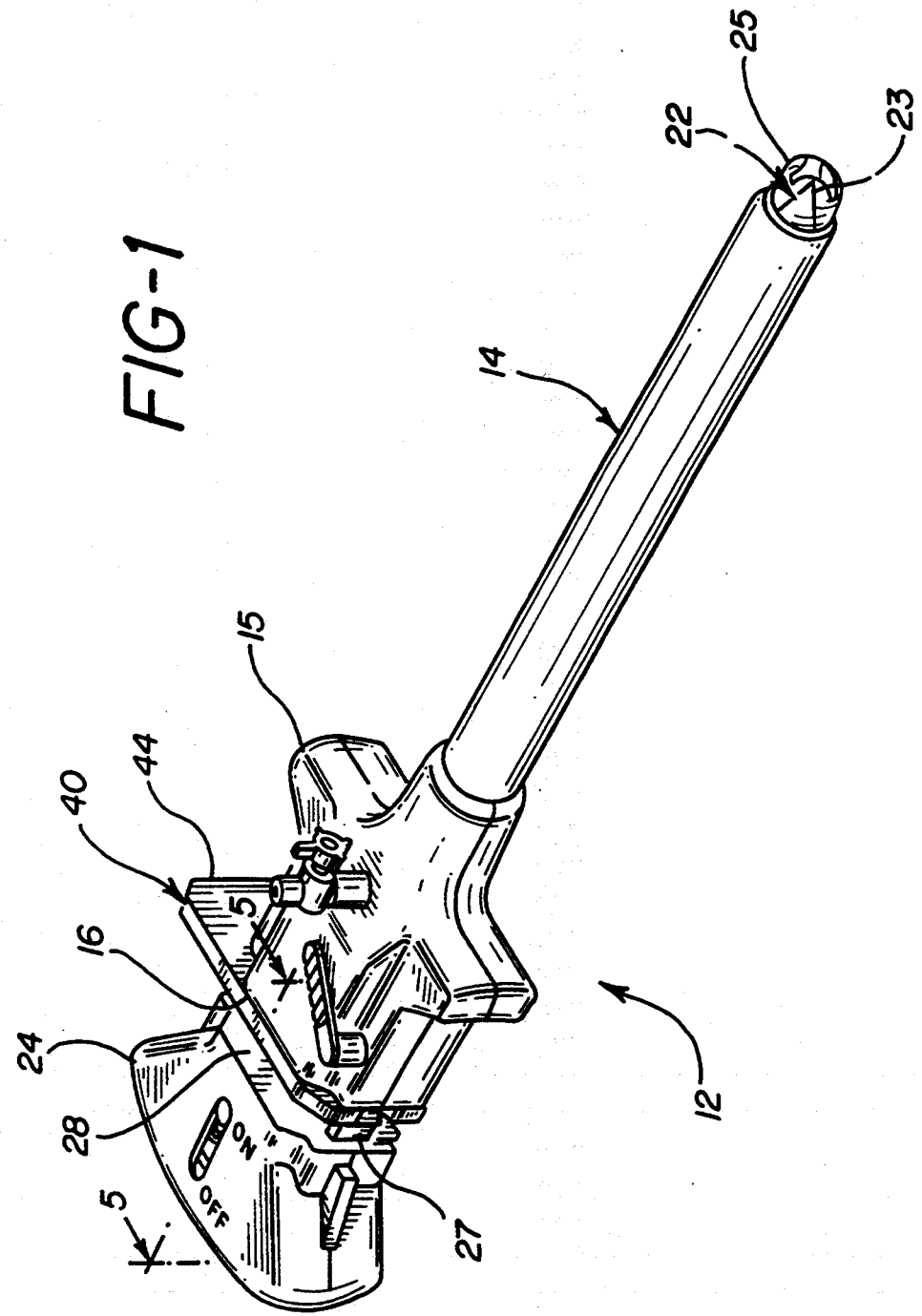

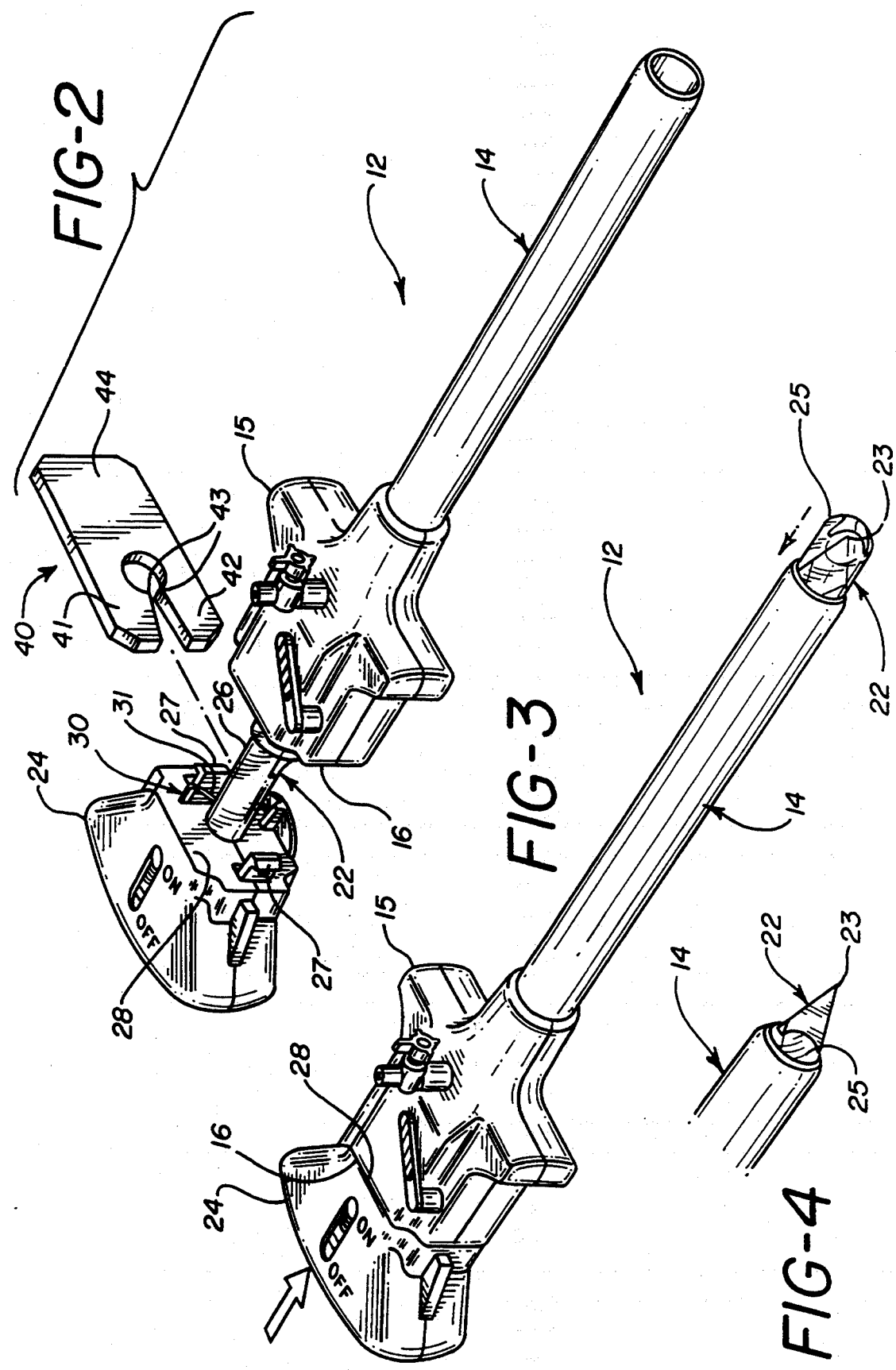

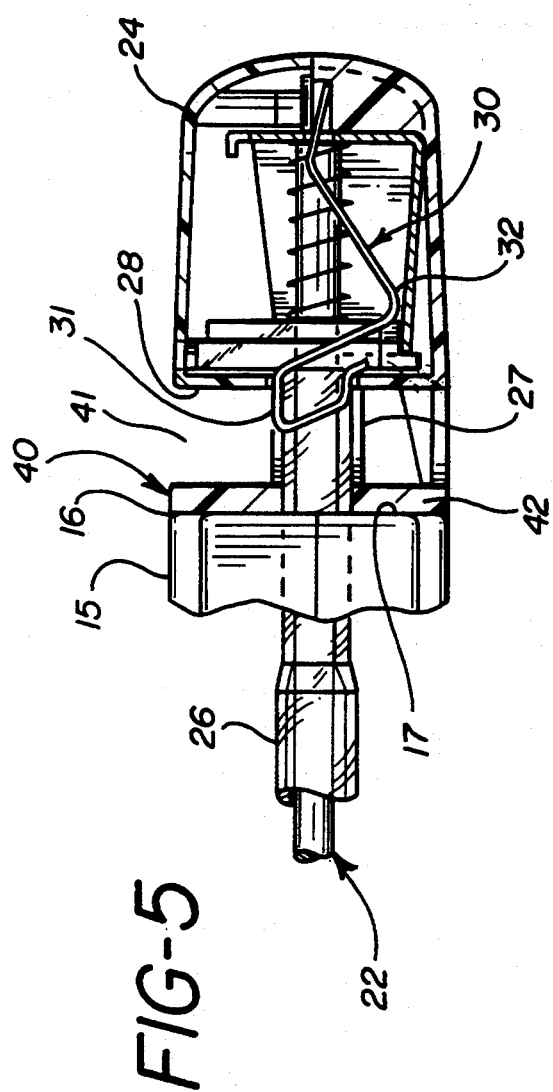
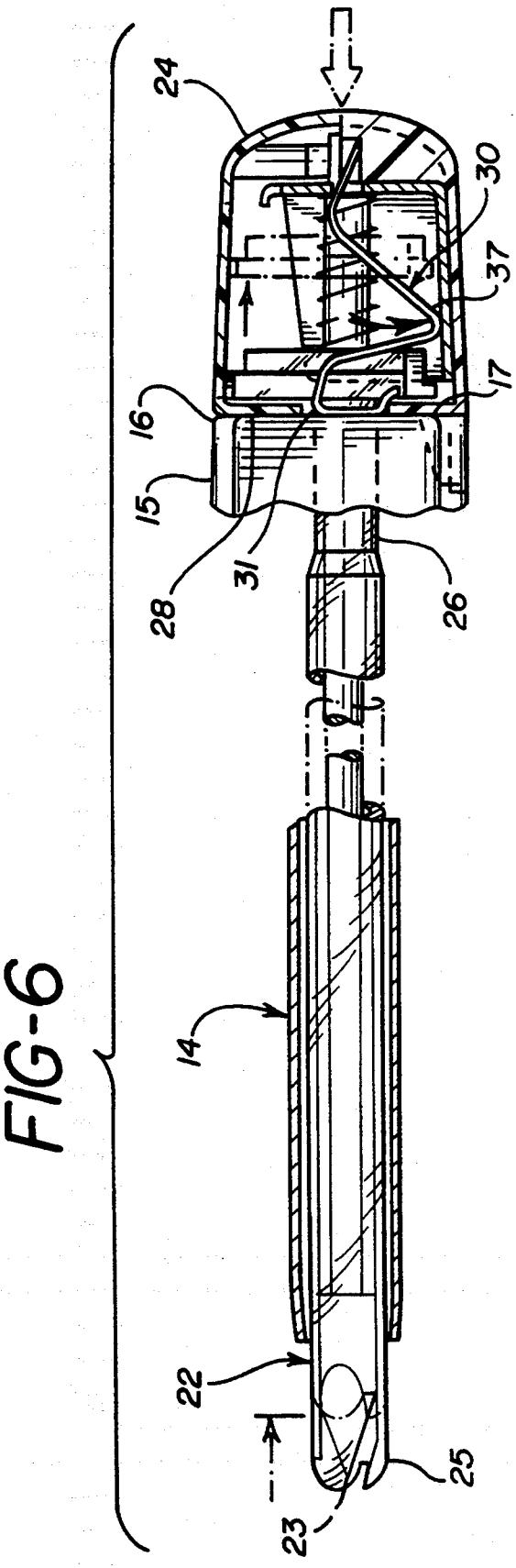
FIG-5
FIG-6

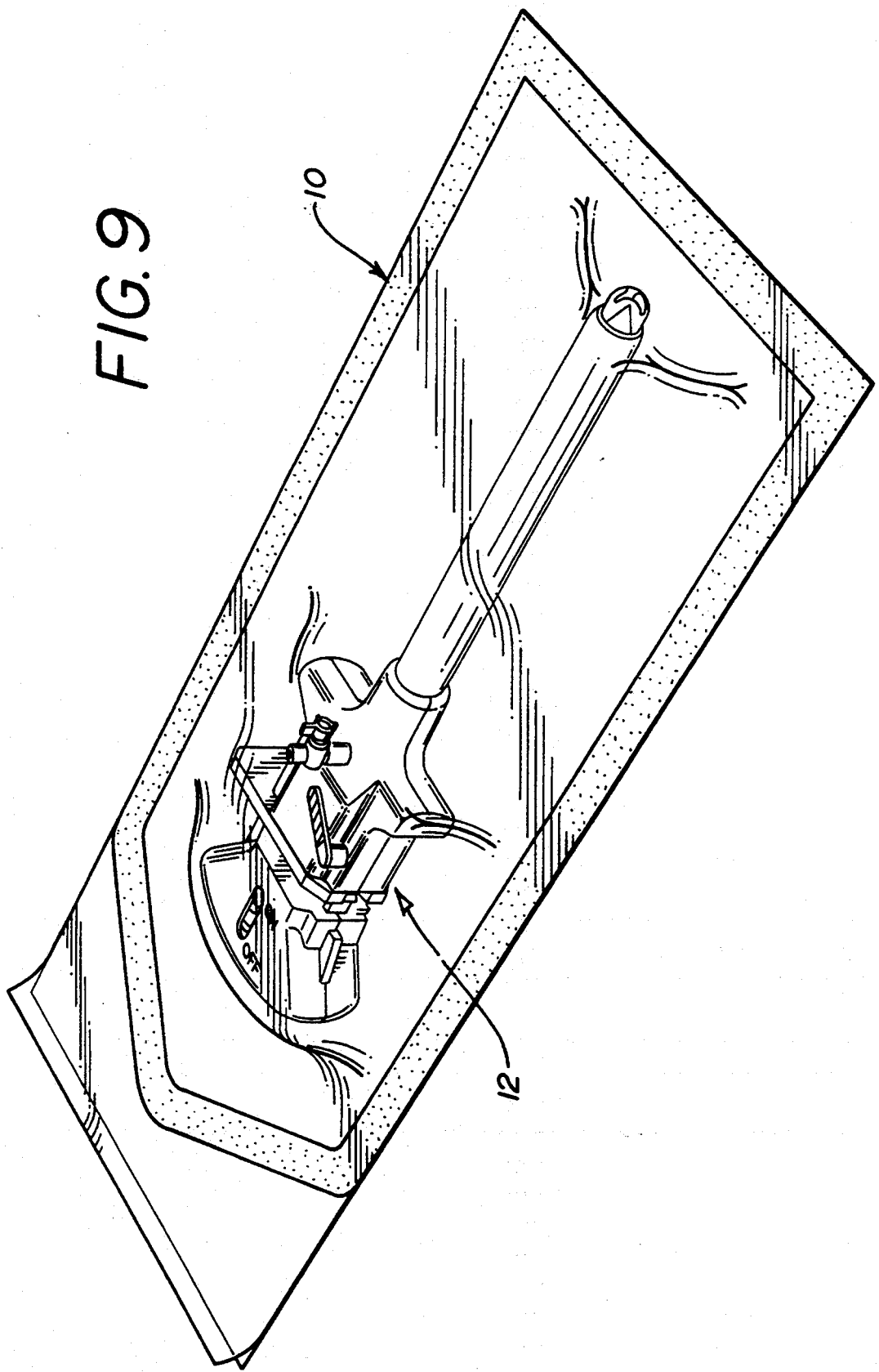

SAFETY INTERPOSER FOR SURGICAL INSTRUMENTS

This is a division of application Ser. No. 08/061,973, filed May 17, 1993, which is hereby incorporated by reference.

FIELD OF THE INVENTION

This invention relates to packaging for use in transportation, handling and storage of surgical instruments including a means to prevent engagement of the surgical instrument or movement of a safety means from a safety position where upon engagement or movement of the instrument, sharp edges or points of the instrument could be exposed.

BACKGROUND OF THE INVENTION

It is important for surgical instruments to be packaged in a readily presentable sterile condition. If the instrument is engaged, particularly if the instrument has sharp edges exposable when engaged, it may disturb the packaging containing the instrument so as to compromise its sterile environment. For example, if a tip of a trocar or an insufflation needle is exposed, it may puncture the packaging.

Flexible packaging is particularly vulnerable to such puncturing or disturbance. Flexible packaging is defined herein as a packaging which does not rigidly conform to the contents of the package. Examples of such packaging are surgical drapes and closed cell foam which may be formed from materials such as, for example, cellulose or plastics. The use of flexible packaging has become increasingly desirable as opposed to thermoformed blister packaging or styrofoam type packaging which have recently become less desirable for reasons relating to economics, ease of packaging disposal in the operating room, processing considerations and environmental concerns.

It is therefore desirable in the sterile packaging of surgical instruments, especially flexible packaging, to prevent unintended engagement of the device or movement of a safety mechanism from its safety position, which could expose a sharp instrument.

A trocar assembly for use in endoscopic surgical procedures generally comprises two major components, an obturator and a cannula. The obturator is initially positioned within the cannula and has a puncturing or penetrating tip which typically extends from the cannula. The obturator tip is used to penetrate the skin and underlying tissue to provide cannula access to a body cavity. The obturator may then be removed and laparoscopic or arthroscopic surgery performed through the cannula. An example of such a device is described in U.S. Pat. No. 4,535,773.

Typically, in transportation and storage as well as in use, the obturator is positioned in the cannula and the puncturing or penetrating tip of the obturator extends from the distal end of the cannula. However, many trocars have safety shields which cover the tip of the obturator. If the trocar is not armed, the safety shield is maintained in its tip covering position. When the trocar assembly is engaged for puncturing, the safety shield can be moved to expose the puncturing or penetrating tip of the obturator.

An example of a means for engagement of the trocar is a safety spring which is actuated by a spring actuating element connected to the distal end of an obturator handle. When the obturator is inserted into the cannula, a portion of the spring actuating element located at the distal end of the obturator handle engageably interacts with the proximal end of a cannula handle to move the safety spring from a first position to a second position. In the second position, the safety shield can then be retracted from its covering position over the obturator tip. An example of such a safety spring is described in U.S. Pat. No. 5,114,407.

It is therefore desirable in the packaging of trocar assemblies to prevent unintended engagement.

A Verress-type or insufflation needle typically comprises a sharp needle having a lumen extending therethrough. An inner needle having a rounded safety tip extends through the lumen and distally beyond the sharp distal needle tip. When the safety tip engages with an outside object, if the force is great enough, the safety tip moves axially and proximally within the needle to expose the sharp needle tip. An example of such a needle is described in U.S. Pat. No. 5,139,485.

It is therefore desirable when packaging a Verress needle to prevent proximal axial movement of the safety tip away from its safety position.

It is also desirable to prevent unintended engagement of surgical instruments to avoid other safety concerns which may be posed by an exposed sharp instruments.

SUMMARY OF THE INVENTION

The present invention provides an interposer means to prevent engagement of a surgical instrument or a corresponding movement of a safety mechanism, to expose a sharp instrument such as a cutting or puncturing instrument, e.g., a trocar tip. More particularly, the present invention provides a safety interposer which may be used for packaging surgical instruments in a sterile packaging environment. The safety interposer acts to prevent coupling or engagement of interactive parts of the instrument or prevent movement of a safety mechanism from a safety position.

In a preferred embodiment of the present invention, a safety interposer is used to prevent coupling of a cannula handle and an obturator handle of a trocar assembly where such coupling acts to engage the trocar assembly. The interposer thereby prevents the trocar obturator from inadvertently extending from its safety shield.

Another feature of the present invention provides a safety interposer with a slotted hole configuration to allow it to fit around the shaft or tubular member of an instrument and to be easily removed by pulling it in a direction approximately perpendicular to the instrument's axis.

In a preferred embodiment of the invention, the safety interposer is shaped to fit around the shaft of the obturator and act as a physical barrier to prevent a spring actuating element located on the distal end of the obturator handle, engaging the cannula handle to thereby permit movement of the safety shield.

In another embodiment a safety interposer may be inserted around the shaft of an inner needle with a safety tip which is inserted into a hollow insufflation needle, to prevent depression of the safety tip to expose the sharp hollow outer needle. A notch is cut through the hollow needle or its housing and into the inner needle. The shaft of the inner needle is adapted to receive the interposer to physically block the tip's longitudinal axial movement with respect to the hollow needle, thereby avoiding exposing the sharp hollow needle tip.

The safety interposer may also be shaped to fit around a tubular member attached to the inner needle with safety tip. The safety interposer is physically removable from the instrument.

DETAILED DESCRIPTION OF THE DRAWINGS

FIG. 1 illustrates a perspective view of an uncoupled trocar assembly with a safety interposer.

FIG. 2 illustrates an exploded perspective view of an uncoupled trocar assembly with a safety interposer.

FIG. 3 illustrates a perspective view of a coupled trocar assembly with the safety mechanism covering the obturator.

FIG. 4 illustrates a partial perspective view of an exposed obturator tip with a retracted safety mechanism.

FIG. 5 illustrates a partial cross sectional view of a trocar assembly with a safety interposer taken along lines 5—5 of FIG. 1.

FIG. 6 illustrates an cross sectional view of a trocar assembly of FIG. 3 with parts broken away.

FIG. 9 illustrates a perspective view of the trocar assembly 12 with a safety interposer as illustrated in FIG. 1, contained in a sterile flexible packaging.

DETAILED DESCRIPTION OF THE PREFERRED EMBODIMENT

Figure 7:
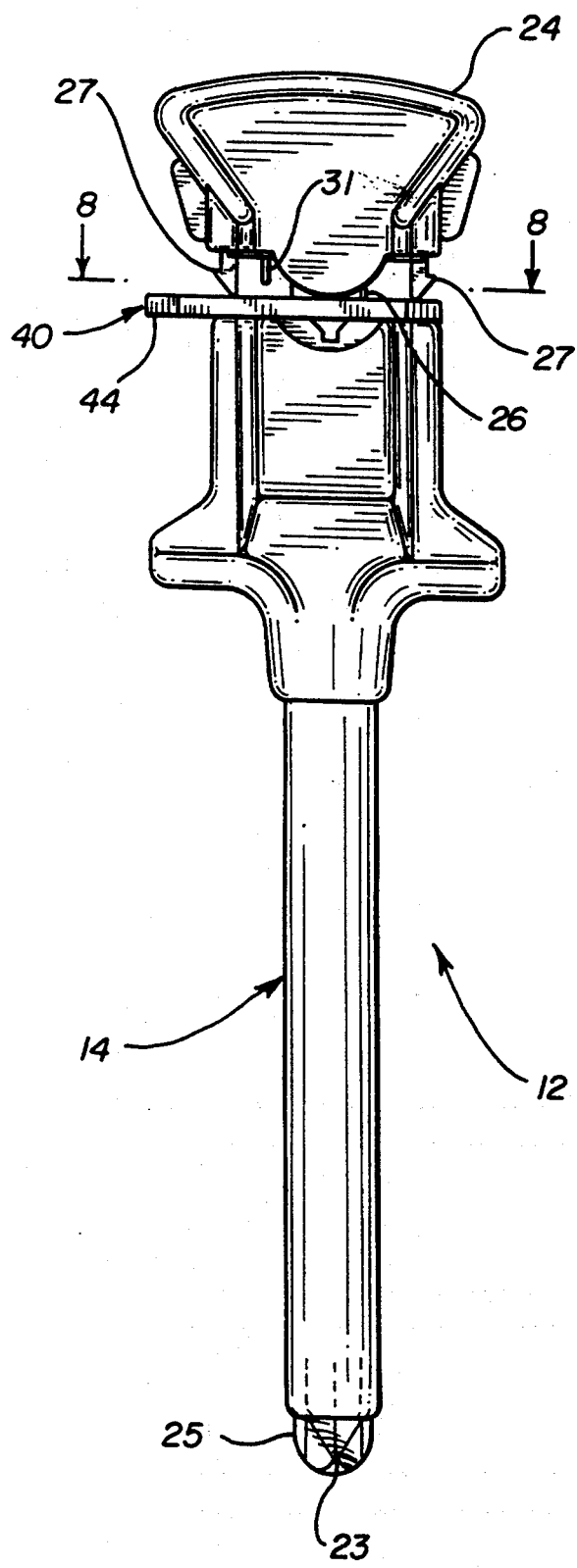
FIG. 7 illustrates a bottom plan view of a safety interposer with a trocar assembly.

Referring now to FIGS. 1-8 there is illustrated a trocar assembly 12 comprising a cannula 14 and an obturator 22. FIG. 9 illustrates the trocar assembly contained in a flexible sterile outer wrap 10. The cannula 14 comprises a cannula handle 15 with a proximal end 16. The proximal end 16 of the cannula handle 15 has an outer circumferential rim 17 which projects proximally outward from the proximal end 16 of the cannula handle 15. The obturator 22 comprises an obturator handle 24, an obturator shaft 26, a puncturing tip 23 and a safety shield 25. The obturator handle 24 comprises a distal end 28 which has coupling means 27 and a safety mechanism 30 comprising a spring actuator 31 and a safety spring 32.

The coupling means 27 may be received by the proximal end 16 of the cannula handle 15 to couple the obturator 22 with the cannula 14. In coupling with the cannula 14, the coupling means 27 extend inside and beyond the rim 17 of the cannula handle 15 towards the end 16.

The safety mechanism 30 is shown in a safety position in FIGS. 1, 2, 5, 7 and 8 and in its released or engaged position in FIGS. 3, 4 and 6 which illustrate a coupled trocar assembly 12. When the trocar assembly 12 is coupled, the rim 17 of the cannula handle proximal end 16 contacts and depresses the spring actuator 31. The depressed spring actuator 31 causes the safety spring 32 to move to release the safety shield 25. A mechanism by which a similar spring actuator operates to release a safety shield is described in U.S. Pat. No. 5,114,407 incorporated herein by reference.

Figure 8:
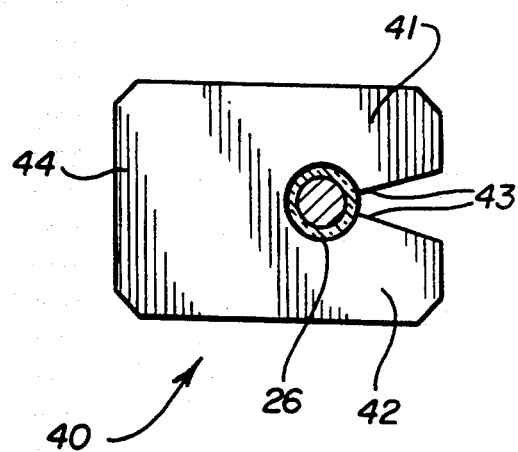
FIG. 8 illustrates a safety interposer of the present invention as seen along line 8—8 of FIG. 7.

Referring now to FIGS. 2 and 8, there is illustrated a safety interposer 40 having a first and a second arm 41 and 42 defining a slot, relatively circular in shape. Each of the first and second arm 41 and 42 has an inwardly projecting element 43 which serves to narrow the slot and close the circle to permit the safety interposer 40 to engage relatively snugly around the obturator shaft 26 (FIG. 8) while not closing completely around the shaft. The slot permits the interposer 40 to be inserted around the shaft 26 and removed when a pulling force, generally perpendicular to the trocar axis, is applied to the interposer 40 on a side 44 opposite the slot. The side 44 projects from the trocar assembly 12 so that a user may grasp the side 44 to remove the interposer 40 from the trocar assembly 12.

The interposer 40 is of sufficient length and width so that when it is inserted between the cannula handle proximal end 16 and obturator handle distal end 24, it contacts the outer circumferential rim 17 extending from cannula handle proximal end 16. The interposer 40 is sufficiently rigid so that it will not displace distally from the rim 17 towards the cannula proximal end 16 to an extent that the rim 17 can depress the spring actuator 31 and engage the safety mechanism 30. Thus the interposer 40 prevents engagement of the trocar.

FIGS. 1, 5 and 7 illustrate a trocar assembly 12 with a safety interposer 40 inserted between the cannula handle 15 and the obturator handle 24. The obturator coupling means 27 extend further distally from the obturator handle 24 than the spring actuator 31. Therefore when the interposer 40 is positioned between the distal end 28 of the obturator handle 20, and the proximal end 16 of the cannula handle, the interposer 40 blocks the coupling means 27 from coupling the obturator 22 with the cannula 14. Because the coupling means 27 extend a greater distance from the distal end 28 of the obturator, the interposer 40 does not come in contact with the spring actuator 31. Thus the interposer 40 creates a physical barrier to prevent depression of the spring actuator 31 which when depressed, releases the safety spring 32 and permit the safety shield 25 to be moved from a protective safety position covering the puncturing tip 23 of the obturator 22 as illustrated in FIGS. 3, 4 and 6.

Although the above description refers to specific uses of the safety interposer with a trocar assembly or an insufflation or Veress-type needle, it is not intended to be limited to the specific embodiment described. For example the interposer may be used with any surgical cutting instrument which has a shaft or tubular member around which the interposer may fit such that the interposer acts as a physical barrier to prevent movement of a safety means from a safety position whereby a sharp edge or point could be exposed or where the interposer acts to prevent engagement of two interactive parts which if engaged would permit exposure of a sharp edge or point.

It may be observed from the above that numerous equivalents or modifications may be made without departing from the spirit and scope of the invention. No limitation to the claimed invention is intended from the specific embodiments described herein.

What is claimed is:

1. A trocar assembly comprising:
   a cannula having: a proximal end and a distal end, the proximal end coupled to a cannula handle having a proximal end;
   an obturator having: a proximal end coupled to an obturator handle having a distal end, a shaft, and a distal end comprising a puncturing tip which is extendable through said cannula and beyond the distal end of said cannula;

a safety shield slidable relative to said obturator shaft and capable of covering the puncturing tip of said obturator, said safety shield coupled to the obturator handle, a safety mechanism coupled to the obturator handle for preventing axial movement of said safety shield relative to said obturator shaft means coupled to said cannula for releasing said safety mechanism by contacting it to permit axial movement of said safety shield to expose the puncturing tip when said obturator handle is coupled to said cannula handle; and an interposer means for physically intercepting said means for releasing said safety mechanism to prevent said means for releasing said safety mechanism from contacting said safety mechanism and preventing coupling of the cannula handle and obturator handle.

2. The trocar assembly of claim 1 wherein said safety mechanism comprises a safety spring and a spring actuator which is positioned on the distal end of the obturator handle so that when said cannula handle and said obturator handle are not coupled together, said safety spring engages said safety shield to prevent axial movement of said safety shield relative to said obturator shaft, and when said interposer means is removed and said obturator and said cannula are coupled for use, the proximal end of the cannula handle interacts with said spring actuator to cause said safety spring to move from a first position to a second position, to allow said safety shield to move axially.

3. The trocar assembly of claim 2 wherein said interposer means is shaped to fit around the shaft of the obturator to intercept communication between said spring actuator and said cannula handle.

4. The trocar assembly of claim 2 wherein said interposer has a slotted hole configuration.

5. The trocar assembly of claim 1 wherein said trocar assembly is contained in a flexible sterile packaging.

* * * * *